United States Patent

Bunyan

[11] Patent Number: 5,951,516
[45] Date of Patent: Sep. 14, 1999

[54] APPLICATOR

[75] Inventor: Glenn Walter Bunyan, Kanwal, Australia

[73] Assignee: N.J. Phillips Pty. Limited, Somersby, Australia

[21] Appl. No.: 09/141,272

[22] Filed: Aug. 27, 1998

[30] Foreign Application Priority Data

Sep. 1, 1997 [AU] Australia ................................. PO8894

[51] Int. Cl.⁶ .......................... A61M 5/155; A61M 5/315
[52] U.S. Cl. ............................................. 604/143; 604/135
[58] Field of Search ................................... 604/135, 136, 604/137, 147, 134, 146, 143, 141

[56] References Cited

U.S. PATENT DOCUMENTS

| | | | |
|---|---|---|---|
| 3,563,098 | 2/1971 | Glex | 604/135 |
| 4,442,836 | 4/1984 | Meinecke et al. | 604/137 |
| 4,487,602 | 12/1984 | Christensen et al. | 604/137 |
| 4,676,781 | 6/1987 | Phillips et al. | 604/136 |
| 4,717,383 | 1/1988 | Phillips et al. | 604/135 |
| 4,787,891 | 11/1988 | Levin et al. | 604/136 |
| 5,122,119 | 6/1992 | Lucas | 604/136 |
| 5,451,210 | 9/1995 | Kramer et al. | 604/136 |
| 5,567,160 | 10/1996 | Massino | 604/135 |

*Primary Examiner*—Paul J. Hirsch
*Attorney, Agent, or Firm*—Ladas & Parry

[57] ABSTRACT

An applicator (10) to deliver a liquid via a needle (20). The applicator (10) includes a shroud (44) which cooperates with a trigger (41) and trigger lock (52) so that the needle (20) is only exposed upon actuation of the trigger (41) and liquid is only injected when the shroud (44) is retracted to a position at which a desired length of the needle (20) has penetrated.

10 Claims, 4 Drawing Sheets

APPLICATOR

TECHNICAL FIELD

The present invention relates to applicators and more particularly but not exclusively to applicators used in delivering a medication to animals.

BACKGROUND OF THE INVENTION

Frequently medication is delivered to an animal via an applicator (ejector), with the applicator having a needle through which the medication passes.

In the environment that the above mentioned applicators is employed, it is not unusual for needlestick injuries to occur.

The above discussed problem is exacerbated where potentially dangerous chemicals are being administered. For example, a dangerous chemical would be a chemical sterilent.

Still further to the above a problem, associated with injection is premature activation of the dosing mechanism or delivery of the dose prior to full needle penetration.

OBJECT OF THE INVENTION

It is the object of the present invention to overcome or substantially ameliorate the above disadvantages.

SUMMARY OF THE INVENTION

There is disclosed herein an applicator comprising:

a body via which a liquid to be injected passes;

a needle mounted on the body and through which the liquid is to be injected;

a retractable shroud movably mounted on the body for movement between an extended position and a retracted position by engagement with a surface through which the needle is to pass, the shroud in its extended position covering said needle while in said retracted position exposing a desired length of said needle;

a trigger mounted on the body and which governs the delivery of liquid to the needle, said trigger being movable between an inoperative position and an operative position at which the liquid is delivered to said needle, said trigger in said inoperative position engaging the shroud to prevent movement thereof from its extended position; and a trigger lock mounted on the body and engaged by the shroud to be moved from a first position to a second position, said trigger lock in said first position engaging said trigger preventing movement thereof to said operative position while in said second position permitting movement of said trigger to said operative position.

BRIEF DESCRIPTION OF THE DRAWINGS

A preferred form of the present invention will now be described by way of example with reference to the accompanying drawings wherein.

DETAILED DESCRIPTION OF THE PREFERRED EMBODIMENTS

Figure 1:
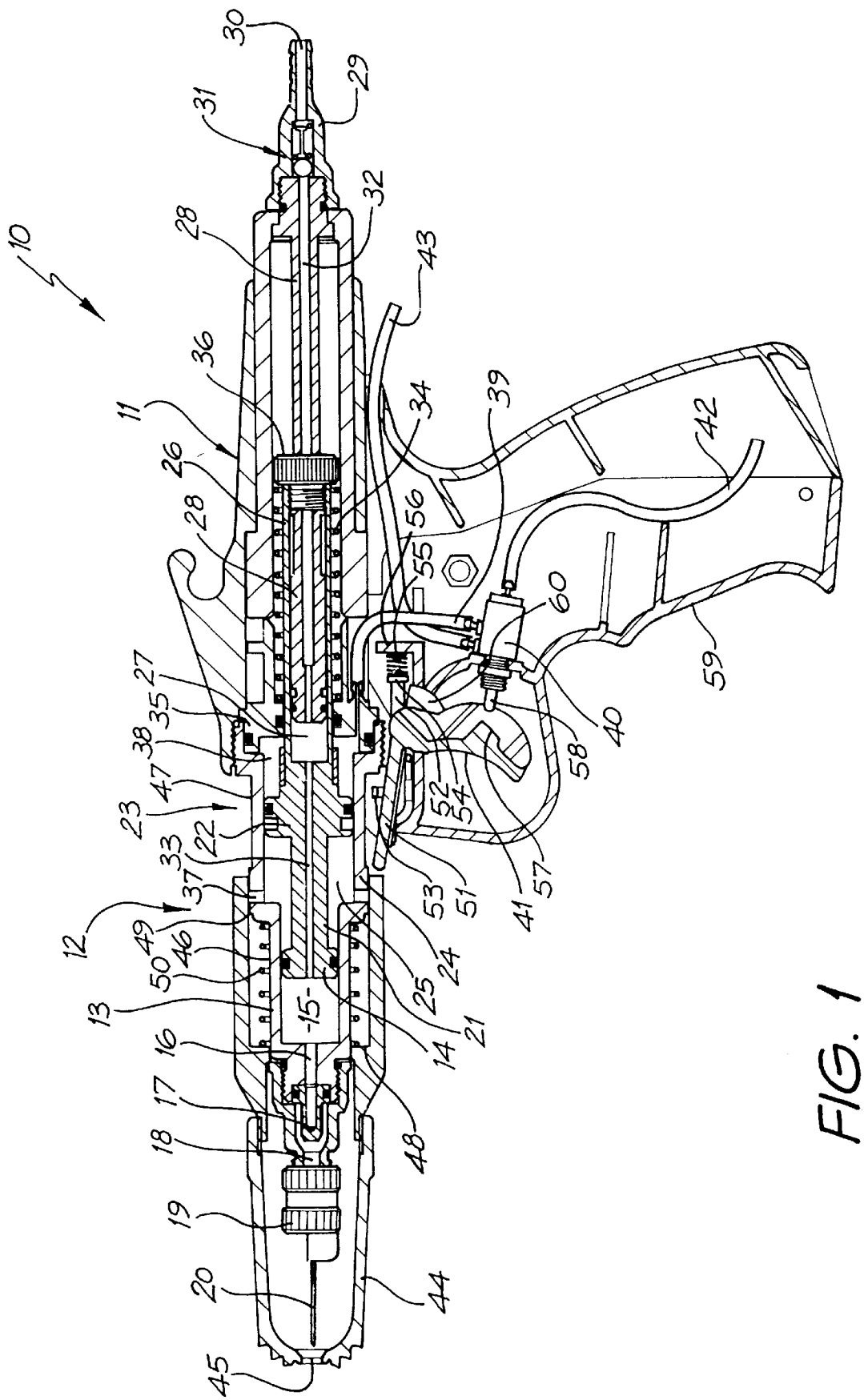
FIG. 1 is a schematic sectioned side elevation of an applicator.
Figure 2:
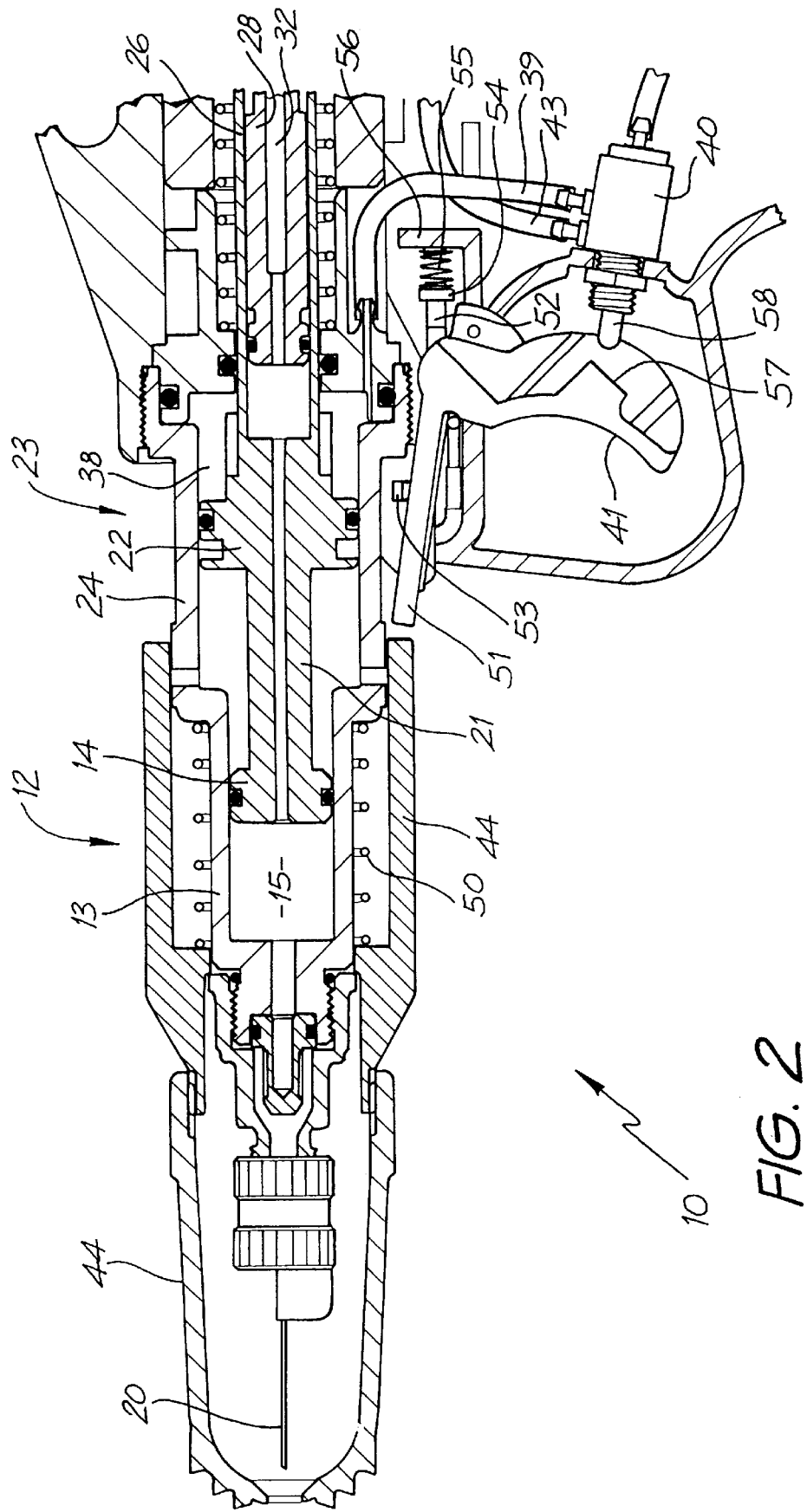
FIG. 2 is an enlarged view of the trigger area of the applicator of FIG. 1.

In the accompanying drawings there is schematically depicted an applicator 10. The applicator 10 includes a body 11 which receives an interacting piston and cylinder assembly 12. The assembly 12 includes a cylinder 13 which cooperates with a piston 14 to generally enclose a variable volume chamber 15. Leading from the chamber 15 is a passage 16 through which the liquid to be injected passes to a one-way valve 17. The one-way valve 17 communicates with a further passage 18 formed by a needle mounting 19. The passage 18 leads to the needle 20. The valve 17 prevents reverse flow from the passage 18 to the passage 16, Extending rearwardly from the piston 14 is a piston rod 21 to which there is attached a further piston 22. The further piston 22 is part of a further piston and cylinder assembly 23. The assembly 23 includes a cylinder 24 which cooperates with the piston 22, cylinder 13 and piston 14 to form a variable volume chamber 25.

Extending rearwardly from the piston 22 is a sleeve 26 having a central passage 27. Slidably mounted in the passage 27 is a shaft 28 extending to an inlet mounting 29. Extending through the inlet mounting 29 is a passage 30 provided with a one way valve 31. Formed in the shaft 28 and extending to the valve 31 is a passage 32, which passage 32 extends to the passage 27.

Extending through the piston 14, piston rod 21 and piston 22 is a passage 33 so that the chamber 15 is in communication with the inlet mounting 29.

The pistons 14 and 22 are urged to move toward the inlet mounting 29 by means of a spring 34, which abuts an internal sleeve 35 and an abutment member 36 secured to an intermediate portion of the shaft 28. The spring 34 thereby urges movement of the pistons 14 and 22 to a position at which the volume of the chambers 15 and 25 is at a maximum. In that regard it should be appreciated that the chamber 25 is vented to atmosphere via passages 37.

The piston 22, cylinder 24 and sleeve 35 cooperate to enclose a variable volume chamber 38. A fluid working (preferably a gas such as compressed air or liquid petroleum gas) is delivered under pressure to the chamber 38 via a duct 39. The duct 39 extends to a valve 40 operated by the trigger 41. When the trigger 41 is pivotally mounted in the body 11 so that when it is depressed it engages the valve 40. The fluid under pressure is then delivered from an inlet duct 43 to the duct 39. This fluid under pressure causes movement of the piston 22 toward the needle 20 thereby reducing the volume of the chamber 15. A liquid (such as a medication) contained in the chamber 15 would then be injected via the needle 20. In that regard it should be appreciated that the inlet mounting 29 would be connected to a flexible tube leading to a reservoir of the liquid to be injected.

When the trigger 41 is released and moved from engagement with the valve 40, the valve 40 connects the duct 39 to an exhaust duct 42. Accordingly, the pressure in the chamber 38 is relieved. The spring 34 then returns the pistons 14 and 22 to their positions at which the volume of the chamber 38 is at its minimum and the volume of the chamber 15 is at its maximum. As the piston 14 moves to maximise the volume of the chamber 15, the liquid to be injected is drawn into the chamber 15 via the passages 32.

The valve 17 and 31 (both being one-way valves) cause the liquid to be injected to move from the inlet mounting 31 to the needle 20.

The safety features of the above described injector 10 are provided by inter-reaction between the shroud 44 and the trigger 41.

Figure 4:
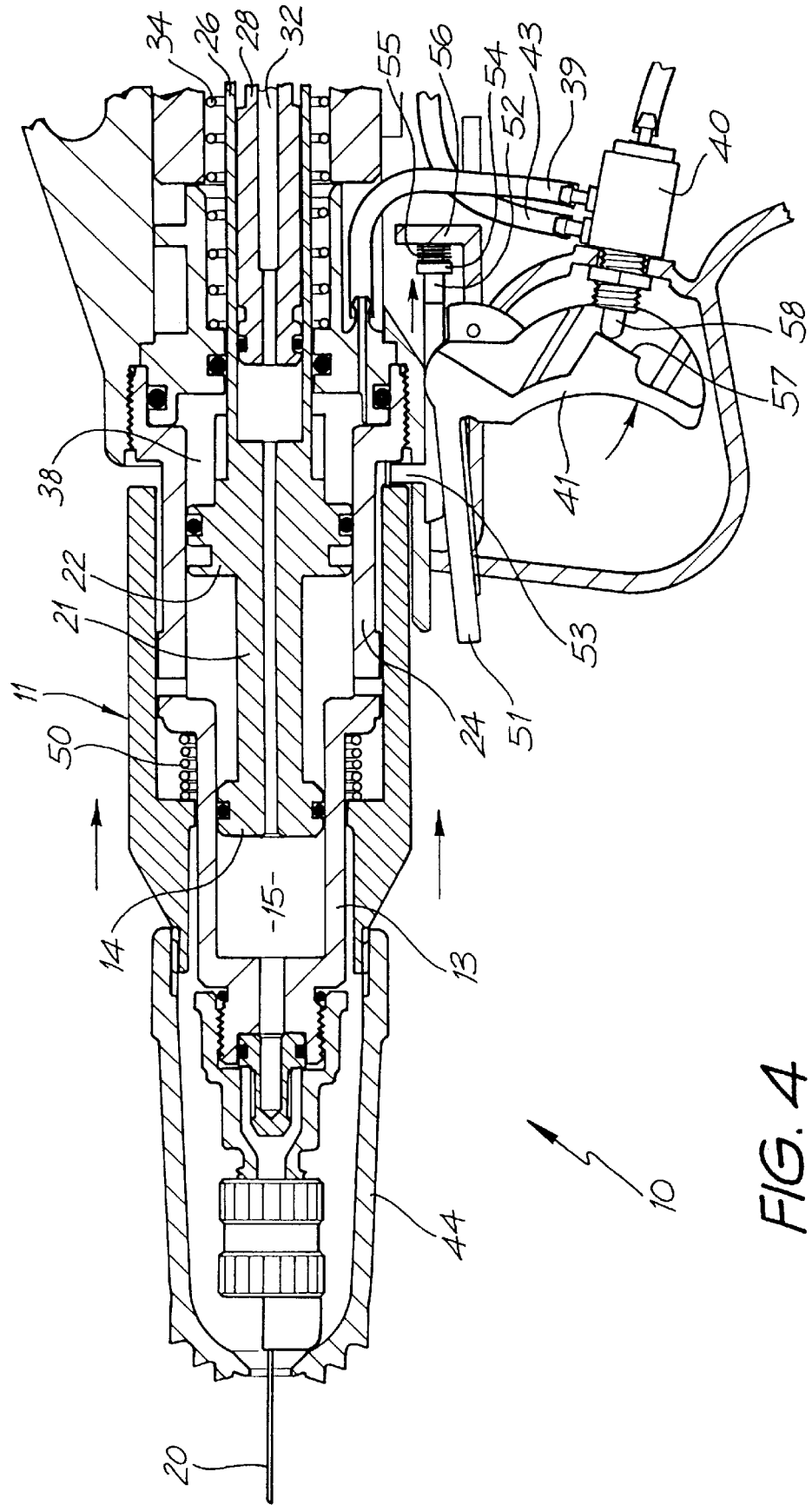
FIG. 4 is a still further enlarged view of the trigger area of the applicator of FIG. 1, with the trigger in a still further operative position.

The shroud 44 is movable from an extended position (as shown in FIG. 1) covering the needle 20 to a fully retracted position (as shown in FIG. 4) exposing a desired length of the needle 20. In that regard it should be appreciated that the shroud 44 has an opening 45 through which the needle 20 projects. Provision of the shroud 44 inhibits needlestick injuries.

The shroud 44 slidably engages cylindrical surfaces 46 and 47 so as to be guided thereby in its movement.

Extending between an abutment face 48 of the shroud 44 and a step 49 in the cylinder 15, is a spring 50 which urges the shroud 44 to its position at which it covers the needle 20 (FIG. 1). In that regard it should be appreciated that apart from the spring 50, the shroud 44 is free to move between its extended and retracted positions. In essence, when the applicator 10 is pushed against a surface through which the needle 20 is to pass, contact with that surface will cause the shroud 44 to move to its retracted position.

The trigger 41 includes a projection 51 which is positionable to abut the rear of the shroud 44. When the shroud 44 is in its extended position and the trigger 41 in its inoperative position, the projection 51 is located behind the shroud 44 and prevents movement of the shroud 44 from its position covering the needle 20. However, upon displacement of the trigger 41 to an intermediate position at which it is not engaged with the valve 40 but having its projection 51 displaced from engagement with the shroud 44, the shroud 44 is then permitted to move rearwardly to its fully retracted position (FIG. 4).

Figure 3:
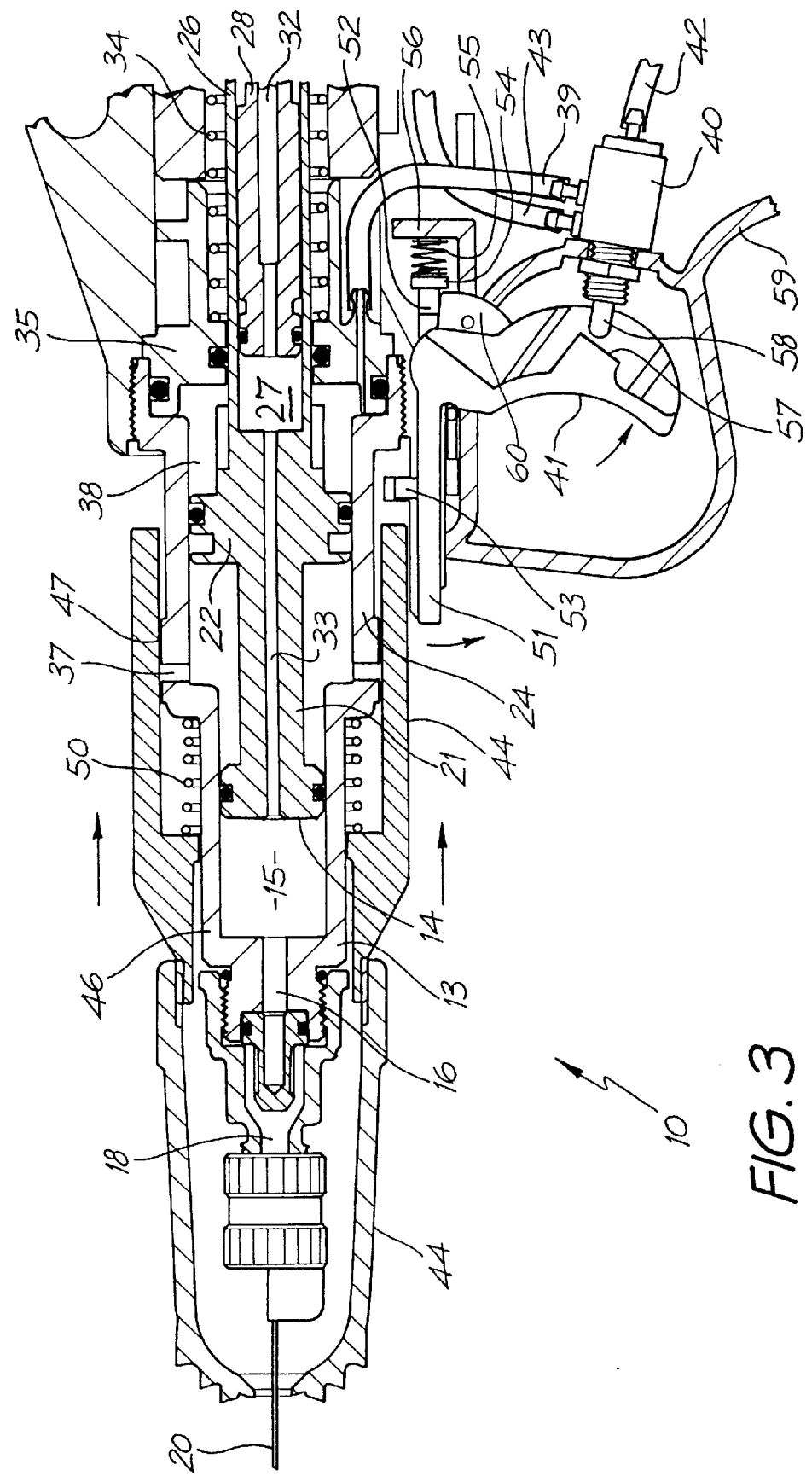
FIG. 3 is a further enlarged view of the trigger area of the applicator of FIG. 1, with the trigger in a further operative position.

Associated with the trigger 41 is a trigger lock 52. The trigger lock 52 prevents movement of the trigger 41 from its intermediate position (FIG. 3) to its operative position engaging the valve 40 (FIG. 4). The trigger lock 52 is mounted in the body 11 so as to be movable linearly from a first position in which it prevents movement of the trigger 41 from the intermediate position (FIG. 3), to a second position (FIG. 4) at which it permits movement of the trigger 41 from its intermediate position to its operative position engaged with the valve 40.

The trigger lock 52 is moved between the first and second positions by engagement with the shroud 44. When the shroud 44 is released for movement by the trigger 41, it moves toward the inlet mounting 41, engaging a projection 53 of the trigger lock 52, so that further movement of the shroud 44 toward the inlet mounting 41 causes movement of the trigger lock 52 to its second position at which the trigger 41 is released. More particularly, the trigger lock 52 has an abutment flange 54 which engages the projection 60 of the trigger 41 when the trigger lock 52 is in its first position. When the trigger lock 52 is in its second position, the flange 54 can no longer engage the projection 60 of the trigger 41 thereby permitting movement of the trigger 41.

A spring 55 urges the trigger lock 52 to its first position. The spring 55 extends between the trigger lock 52 and a flange 56 of the body.

The trigger 41 has an abutment portion 57 which is aligned with and bought into engagement with the shaft 58 of the valve 40, which shaft 58 causes operation of the valve 40 to connect the duct 39 with the duct 42 or the duct 43.

Operation of the above described applicator is as follows.

Initially, the chamber 15 would be charged with the liquid to be injected. An operator of the applicator 10 grips the applicator 10 via the handle 59 and has a finger paused for engagement with the trigger 41. The trigger 41 is then engaged and pivoted to its intermediate position freeing the shroud 44 for movement. The applicator 10 is then pressed against the skin surface of the animal to be injected. Force applied to the applicator 10 causes retraction of the shroud 44 (due to engagement with the skin surface) to a position at which it engages the projection 53 and moves the trigger lock 52 to its second position releasing the trigger 41.

Continued pressure applied to the trigger 41 moves the trigger 41 into operative engagement with the valve 40. The valve 40 then enables the fluid under pressure to be delivered to the chamber 38. This then causes movement of the piston 22 and therefore movement of the piston 14 to reduce the volume of the chamber 15. The liquid to be injected in the chamber 15 is then forced out through the now embedded needle 20. Upon release of the trigger 41, the fluid under pressure in the chamber 38 is placed in communication with the exhaust duct 42. The spring 26 then returns the pistons 14 and 22 towards their position at which the chamber 15 is at its maximum volume. At this time, the increase in the volume of the chamber 15 draws in fresh liquid to be injected. When the applicator 10 is pulled away from the skin surface of the animal, the shroud 44, under the influence of the spring 50, resumes its position covering the needle 20.

Safety features in respect of the above mentioned applicator 10 included:

(1) coverage of the needle 20 via the shroud 44;

(2) engagement of the projection 51 with the shroud 44 preventing movement of the shroud 44 until the trigger 41 is moved;

(3) preventing movement of the trigger 41 into engagement with the valve 40 until the needle 20 has reached a desired depth, as the shroud 44 must be retracted sufficiently to move the trigger lock 52 to its second position permitting movement of the trigger 41 to engage with the valve 40; and (4) prevent premature operation of the trigger 41 until the shroud 44 has been retracted by having the needle 20 penetrate a desired depth.

I claim:

1. An applicator comprising:

a body via which a liquid to be injected passes;

a needle mounted on the body and through which the liquid is to be injected;

a retractable shroud movably mounted on the body for movement between an extended position and a retracted position by engagement with a surface through which the needle is to pass, the shroud in its extended position covering said needle while in said retracted position exposing a desired length of said needle;

a trigger mounted on the body and which governs the delivery of liquid to the needle, said trigger being movable between an inoperative position and an operative position at which the liquid is delivered to said needle, said trigger in said inoperative position engaging the shroud to prevent movement thereof from its extended position; and a trigger lock mounted on the body and engaged by the shroud to be moved from a first position to a second position, said trigger lock in said first position engaging said trigger preventing movement thereof to said operative position while in said second position permitting movement of said trigger to said operative position.

2. The applicator of claim 1, wherein the trigger is moved from said inoperative position thereof by an operator, to release the shroud, and is retained in an intermediate position by said trigger lock being located in the trigger lock first position, with the trigger being moved to the trigger operative position when the shroud is moved to the retracted position thereof to thereby move the trigger lock to the second position thereof.

3. The applicator of claim 2, further including a first interacting piston and cylinder cooperating to provide a first variable volume chamber, a passage extending from said chamber to said needle, a one way valve in said passage restricting the liquid to pass from said chamber to said needle, a passage extending to said chamber to deliver the liquid thereto, a second interacting piston and cylinder cooperating to provide a second variable volume chamber, valve means operable to deliver and exhaust a working fluid with respect to said second chamber, a piston rod connecting the first and second pistons so that said first piston is driven by said second piston, and wherein said trigger is operatively associated with said valve means so that when said trigger is in the operative position thereof, said valve means operates said second piston to move the first piston to eject the liquid through the needle, while said trigger in said inoperative position causes the valve means to operate said second piston to move said first piston to draw liquid into the first chamber.

4. The applicator of claim 3, wherein said second chamber is at a maximum volume when said first chamber is at a minimum volume.

5. The applicator of claim 4, further including a spring urging said second piston to move to a position at which said second chamber is at a minimum volume and wherein said valve means delivers the working fluid under pressure to said second chamber, when said trigger is moved to the operative position thereof.

6. The applicator of claim 5, further including an interacting shaft and sleeve operatively associated with the second piston and extending to a liquid inlet of the body through which the liquid is delivered to said first chamber.

7. The applicator of claim 6, wherein said shaft is fixed to said body, and said sleeve is fixed to said second piston, with a passage extending from said inlet through said shaft, said sleeve, said second piston and first piston to deliver the liquid to said first chamber.

8. The applicator of claim 7, further including a one way valve at said liquid inlet restricting fluid to flow to said first chamber.

9. The applicator of claim 3, wherein said trigger lock includes an is abutment to engage the trigger to define the intermediate position thereof, with abutment being moved to a position releasing the trigger when the trigger lock is moved to the second position thereof.

10. The applicator of claim 9, wherein said piston is pivotably mounted in said body, and said trigger lock is mounted for linear movement in said body, and said applicator further includes a spring urging said trigger lock to the first position thereof.

\* \* \* \* \*